United States Patent
Yokota et al.

(10) Patent No.: US 7,238,803 B2
(45) Date of Patent: Jul. 3, 2007

(54) METHOD FOR PRODUCING EPSILON-CAPROLACTAM

(75) Inventors: Masashi Yokota, Niihama (JP); Yoshinori Kobayashi, Niihama (JP); Masaru Kitamura, Niihama (JP)

(73) Assignee: Sumitomo Chemical Company, Limited, Osaka (JP)

( * ) Notice: Subject to any disclaimer, the term of this patent is extended or adjusted under 35 U.S.C. 154(b) by 187 days.

(21) Appl. No.: 10/883,822

(22) Filed: Jul. 6, 2004

(65) Prior Publication Data

US 2005/0010020 A1   Jan. 13, 2005

(30) Foreign Application Priority Data

Jul. 8, 2003   (JP) .............................. 2003-193390

(51) Int. Cl.
*C07D 201/04*   (2006.01)
(52) U.S. Cl. .................................................... 540/536
(58) Field of Classification Search .................. 540/536
See application file for complete search history.

(56) References Cited

U.S. PATENT DOCUMENTS

| 5,328,720 A | 7/1994 | Emken et al. |
| 5,866,708 A | 2/1999 | Shimizu et al. |
| 5,891,401 A | 4/1999 | D'Acierno et al |

FOREIGN PATENT DOCUMENTS

| EP | 1 028 108 A1 | 8/2000 |
| GB | 1 530 845 | 11/1978 |
| RU | 2 162 197 C2 | 1/2001 |

OTHER PUBLICATIONS

Chemical Machine Technology, 202-204, No. 18, (1965).

*Primary Examiner*—Bruck Kifle
(74) *Attorney, Agent, or Firm*—Foley & Lardner LLP

(57) ABSTRACT

$\epsilon$-Caprolactam is produced by the method comprising the step of introducing a gas comprising cyclohexanone oxime into a layer of solid catalyst particles through a plurality of holes of a gas diffusion plate so that the solid catalyst particles are brought into contact with the gas, while fluidizing the catalyst layer, wherein the holes have an average diameter of about 3 mm or smaller. In accordance with the production method, $\epsilon$-caprolactam can be produced from a raw material gas comprising cyclohexanone oxime with a high conversion of cyclohexanone oxime and a high selectivity to $\epsilon$-caprolactam.

5 Claims, 3 Drawing Sheets

METHOD FOR PRODUCING EPSILON-CAPROLACTAM

BACKGROUND OF THE INVENTION

1. Field of the Invention

The present Invention relates to a method for producing ε-caprolactam, and more particularly relates to a method for producing ε-caprolactam by fluidizing a layer of catalyst particles so as to bring a gas containing cyclohexanone oxime into contact with the catalyst particles.

2. Related Art

ε-Caprolactam is useful as a raw material for nylon or the like. Japanese Patent Application Laid-Open No. 2000-229939 discloses a method for producing ε-caprolactam, by using so-called fluidized bed reaction apparatus, in that a raw material gas containing cyclohexanone oxime is supplied to a catalyst layer having solid catalyst particles so as to bring the raw material gas into contact with the catalyst particles, while maintaining the catalyst layer in a fluidized state. A fluidized-bed reaction apparatus is known, such as an apparatus equipped with a porous gas diffusion plate and having a catalyst layer of solid catalyst particles on the plate. The apparatus can be employed so that the raw material gas is supplied to the catalyst layer through a large number of the holes formed in the porous gas diffusion plate, while maintaining the catalyst layer in the fluidized state. The raw material gas is brought into contact with the solid catalyst particles in the catalyst layer, which is in the fluidized state, to provide a reaction gas containing a product (ex., ε-caprolactam). Conventionally, the fluidized-bed reaction apparatus has a porous gas diffusion plate with the average diameter of the holes of 6 mm or larger, or at least 4–5 mm, in order to supply the raw material gas easily and not to plug the holes.

However, the production method using the conventional fluidized-bed reaction apparatus has problems such that conversion of the raw material (ex. cyclohexanone oxime) and selectivity to the product (ex., ε-caprolactam) are insufficient.

With objects of solving the problems, especially when using cyclohexanone oxime as a raw material, the production method of ε-caprolactam has been researched. As a result, inventors of the present invention have found that the size of the holes in the porous gas diffusion plate of the fluidized-bed reaction apparatus is related with the conversion of the raw material, cyclohexanone oxime, and the selectivity to the product, ε-caprolactam. Based on such findings, the present invention has been accomplished.

SUMMARY OF THE INVENTION

The present invention provides a method comprising the step of introducing a gas comprising cyclohexanone oxime into a layer of solid catalyst particles through a plurality of holes of a gas diffusion plate so that the solid catalyst particles are brought into contact with the gas, while fluidizing the catalyst layer, wherein the holes have an average diameter of about 3 mm or smaller. The method may be carried out using a reaction apparatus equipped with a porous gas diffusion plate having a large number of holes with an average diameter of about 3 mm or smaller and having a layer of solid catalyst particles placed on the plate, so that a raw material gas containing cyclohexanone oxime is supplied through the holes of the porous gas diffusion plate to the catalyst layer so as to bring the raw material gas into contact with the solid catalyst particles while fluidizing the catalyst layer.

DETAILED DESCRIPTION OF THE INVENTION

In the present invention, ε-caprolactam can be produced in a method comprising the step of introducing a gas comprising cyclohexanone oxime into a layer of solid catalyst particles through a plurality of holes of a gas diffusion plate so that the solid catalyst particles are brought into contact with the gas, while fluidizing the catalyst layer, wherein the holes have an average diameter of about 3 mm or smaller. The method may be carried using a reaction apparatus equipped with a porous gas diffusion plate and having a catalyst layer.

Figure 1:
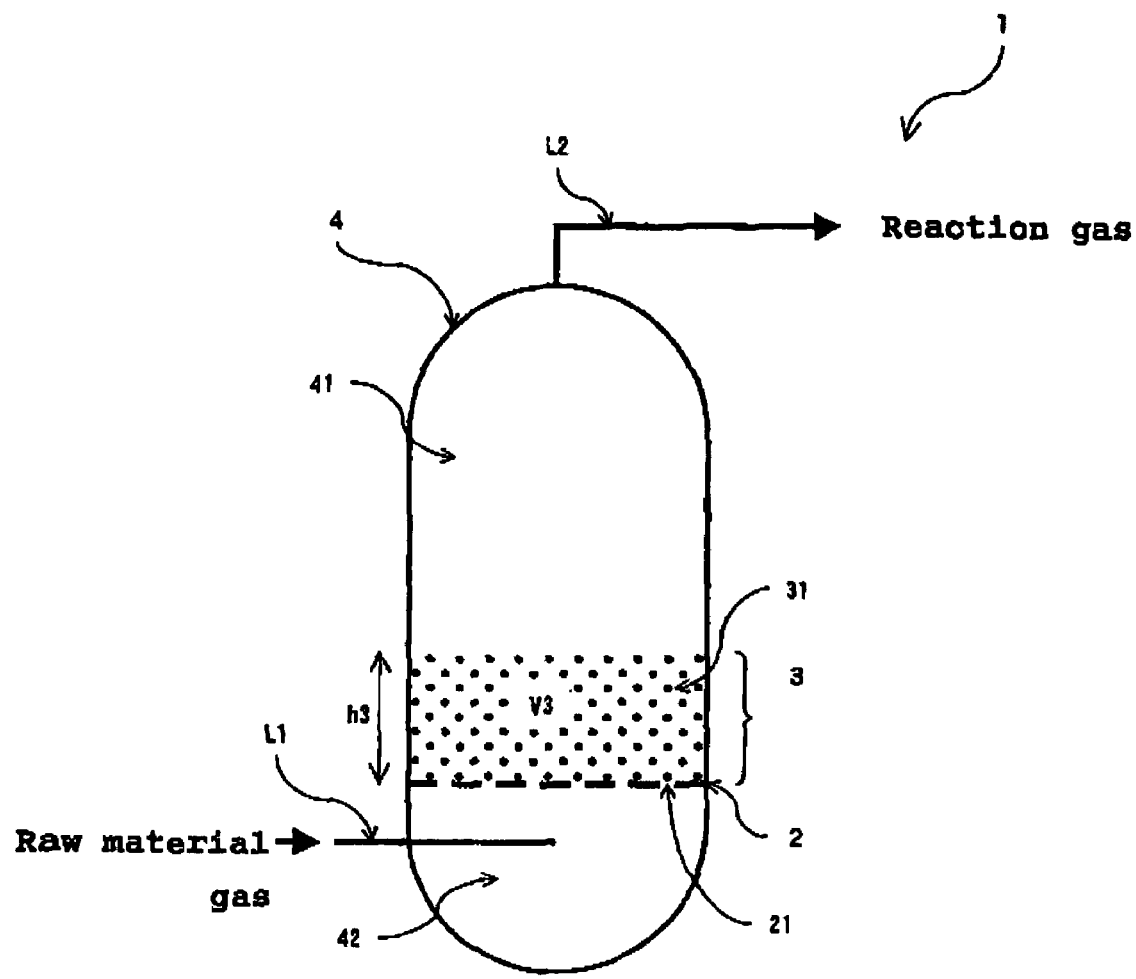
FIG. 1 is a schematic cross-sectional view showing one example of production apparatus which may be employed for a production method in the present invention.

Referring to FIG. 1, one embodiment of the method in the present invention is described below, which should not be construed as a limitation upon the scope of the present invention.

Reaction apparatus 1 (shown in FIG. 1) has reactor 4 and are provided with porous gas diffusion plate 2. More specifically, reaction apparatus 1 has porous gas diffusion plate 2 installed in reactor 4, which is divided into upper section 41 and lower section 42 by porous gas diffusion plate 2. In the reactor, catalyst layer 3 is formed in the upper section 41. Porous gas diffusion plate 2 is plate-like member having a large number of holes 21, and a raw material gas is supplied to catalyst layer 3 through holes 21.

A large number of holes 21 may be formed in porous gas diffusion plate 2. The diameter (d21) of holes 21 maybe about 3 mm or smaller on the average. The average diameter is preferably about 0.5 mm or larger, and is more preferably about 1 mm or larger. When the diameter is smaller than about 0.5 mm, the supply of the raw material gas tends to be insufficient. Also, in terms of formation of holes, the holes preferably have a diameter of about 0.5 mm or larger.

Figure 2A:
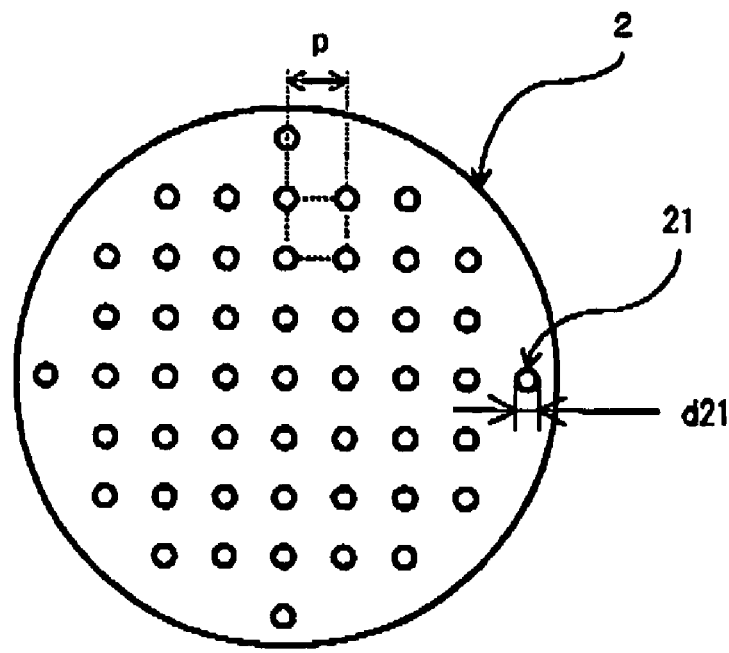
FIG. 2a and FIG. 2b are schematic top-face views showing arrangement of holes in porous gas diffusion plates which may be employed for a production method in the present invention.
Figure 2B:
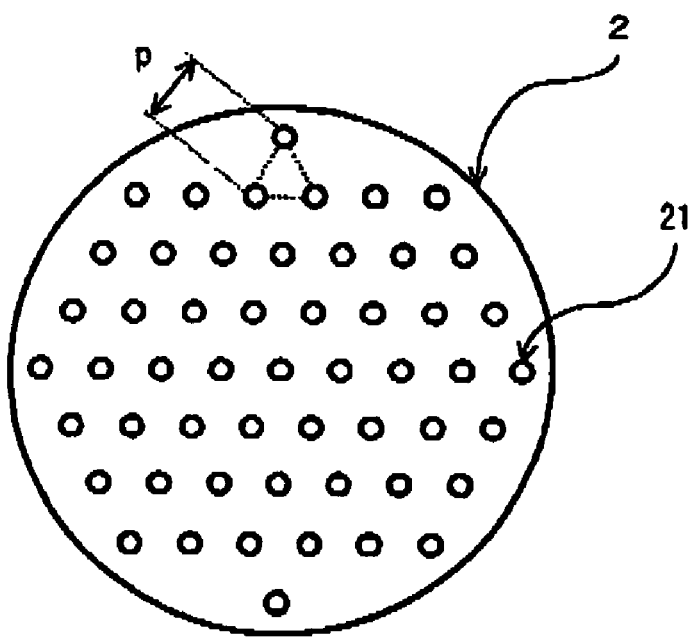

Preferably, the holes 21 in porous gas diffusion plate 2 are arranged so that the respective holes are positioned at the apexes of squares (square arrangement: see, FIG. 2a showing a schematic top-face view of the arrangement) or at the apexes of regular triangles (triangular arrangement see, FIG. 2b showing a schematic top-face view of the arrangement). The holes 21 are preferably formed so that each of them is arranged with a constant interval between them. Intervals (p) between mutually neighboring holes may be about 0.5 cm or longer (and is preferably about 1 cm or longer), and may be about 25 cm or shorter (and is preferably 6 cm or shorter). The rate of the total open surface area of holes in porous gas diffusion plate to the total surface area including holes of the plate may be in the range of from about 0.2% to about 1%.

Figure 3A:
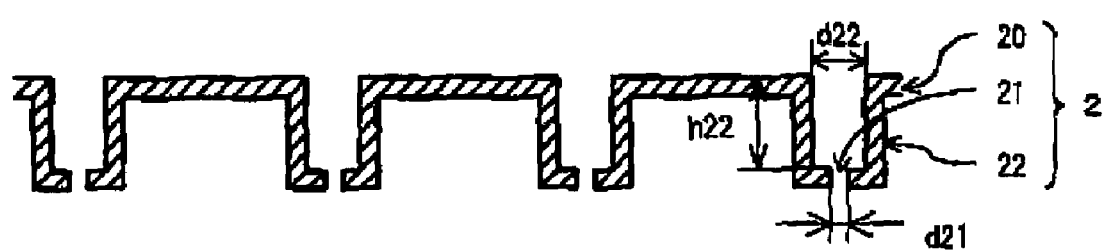
FIG. 3a and FIG. 3b are schematic cross-sectional views showing structure of porous gas diffusion plates which may be employed for a production method in the present invention.
Figure 3B:
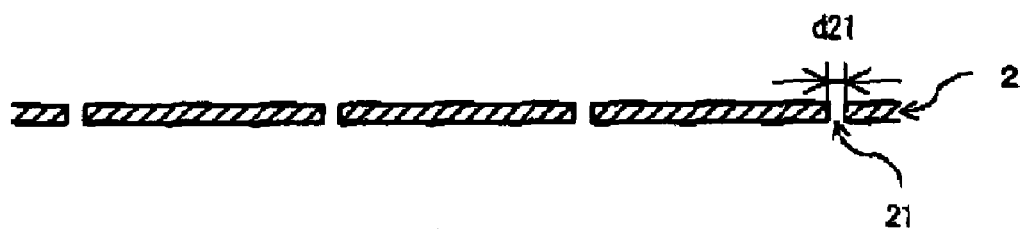

Porous gas diffusion plate 2 may be in the flat shape (see, FIG. 3b showing a schematic cross-sectional view of the structure of the plate). Alternatively, porous gas diffusion plate 2 may have a shape such that cylindrical shrouds 22 are formed so as to be extended downward from plate-like main body 20 of the gas diffusion plate and have holes 21 In the tip ends of the shrouds 22 (see, FIG. 3a showing a schematic cross-sectional view of the structure of the plate). The latter porous gas diffusion plate is preferably utilized In the present invention.

In the latter porous gas diffusion plate, the shrouds 22 may have a cylindrical shape with a circular cross section, or may have a shape with a rectangular cross section. Depth (h22) of the shrouds may be about 5 mm to about 30 mm. Inner diameter (d22) of the shrouds may be equal to or larger than the diameter (d21) of the holes formed in the tip ends of the shrouds. Specifically, inner diameter (d22) of the shrouds may be in the range of from about 2 mm to about 10 mm, while the diameter (d21) of the holes is in the range of about 3 mm or smaller on the average. The inner diameter (d22) of the shrouds may be appropriately decided so that the supply rate of the raw material to the catalyst layer is in the range of from about 20 m/s to about 30 m/s. As described above, the latter porous gas diffusion plate has shrouds 22 with holes 21 formed at the tip ends of the shrouds, thereby lowering the wear degree of catalyst particles in the catalyst layer placed on the place.

In reaction apparatus 1 shown in FIG. 1, catalyst layer 3 of solid catalyst particles 31 may be provided on porous gas diffusion plate 2 in the upper section 41 of reactor 4. Preferable solid catalyst particles are particles mainly containing a zeolite. Examples of particles containing zeolite include particles of pentasil-type zeolites (such as MFI zeolite) and particles of Y-type zeolite particles. Alternatively, the solid catalyst particles may be boric acid type catalyst particles, silica-alumina type catalyst particles, solid phosphoric acid catalyst particles, and crystalline aluminosilicate catalyst particles. These solid catalyst particles can be obtained in known methods. (See, for example, Japanese Patent Application Laid-Open No. (JP-A-)2000-229939 as to pentasil-type zeolite particles; Journal of Catalysis, 6247 (1966) as to Y-type zeolite particles: JP-A-53-37686 and JP-A-46-12125 as to boric acid type catalyst particles; British Patent No. 881927 as to silica-alumina type catalyst particles; British Patent No. 881956 as to solid phosphoric acid catalyst particles; JP-A-57-139062 as to crystalline aluminosilicate catalyst particles.) Among them, pentasil-type zeolites particles (especially, MFI zeolite particles) are preferred.

The particle diameter of solid catalyst particles 31 may be in the range of from about 1 μm to about 200 μm. Preferably, about 90% by weight or more of the solid catalyst particles (and more preferably the entire amount (100% by weight) of the particles) have a particle diameter of about 5 μm to about 100 μm (and more preferably have a particle diameter of about 10 μm to about 100 μm).

Solid catalyst particles 31 may be packed on porous gas diffusion plate 2. Catalyst layer 3 comprises such packed solid catalyst particles 31.

In the production method of the present invention, the raw material gas is brought into contact with solid catalyst particles. In the method, the above-described reaction apparatus 1 may be employed. The raw material gas may be a gas comprising cyclohexanone oxime. Examples of the raw material gas include a pure cyclohexanone oxime gas, a gas containing cyclohexanone oxime which is diluted with an inert gas or other gases; and the like. Examples of the inert gas include a nitrogen gas and an argon gas. Examples of the other gases include a gas having a boiling point lower than that of cyclohexanone oxime. Specifically, examples of the gases include gases of saturated alcohols with 1 to 8 carbon atom(s) such as methanol, ethanol, n-propanol, isopropanol, t-butanol, 1-hexanol, and 1-octanol; and gases of aromatic hydrocarbons such as benzene and toluene.

In the present invention, the raw material gas may be supplied to catalyst layer 3 through holes 21 of porous gas diffusion plate 2. In providing the raw material gas to the catalyst layer 3, the raw material gas may be supplied through a pipe L1 to lower section 42 under porous gas diffusion plate 2 in the reactor 4, as shown in FIG. 1. The inner diameter of reactor 4 may be in the range of from about 500 mm to about 10,000 mm. The height of reactor 4 may be in the range of from about 3,000 mm to about 20,000 mm. The raw material gas may be supplied while being pressurized. The pressure is not particularly limited, as long as it is sufficient to supply the gas to catalyst layer 3. Preferably, the pressure is about 0.1 MPa (1 kgf/cm$^2$) or lower in terms of gauge pressure on the basis of the atmospheric pressure. The raw material gas may be supplied at a temperature of about the same or lower than the temperature for reaction (mentioned below). For example, in the case of using zeolite catalyst particles as the solid catalyst particles 31, the reaction temperature may be in the range of from about 250° C. to about 450° C. and is preferably in the range of from about 300° C. to about 400° C., while the temperature of the raw material gas to be supplied maybe in the range of from about 130° C. to 400° C. and is preferably in the range of from about 250° C. to 380° C.

In the production method of the present invention, the raw material gas is brought into contact with solid catalyst particles 31, while the catalyst layer 3 of the particles is fluidized. For example, solid catalyst particles 31 of the catalyst layer may be blown up by supplying the raw material gas to catalyst layer 3 through the holes (21) so as to fluidize the catalyst layer 3. The conditions for preparing the fluidizing state, such as the amount of the raw material gas to be supplied, the pressure for the supply, the interval (p) among the holes 21 of the porous gas diffusion plate 2, the number of the holes 21, and the volume (V3) of the catalyst layer 3, the height (h3) of the catalyst layer 3 and the like, may be selected properly in order to sufficiently blow up solid catalyst particles 31. The height (h3) of the catalyst layer 3 (at rest) may be in the range of from about 10 cm to about 70 cm.

As described above, in the present invention, the raw material gas comprising cyclohexanone oxime is supplied through the holes 21 Into catalyst layer 3 of catalyst particles 31, while fluidizing the catalyst layer, so as to be brought into contact with the solid catalyst particles 31 in the catalyst layer 3. As a result, the cyclohexanone oxime contained in the raw material gas is subjected to rearrangement reaction to produce ε-caprolactam. Thus produced ε-caprolactam may be obtained in the resulting reaction gas, which may be discharge to the outside of reactor 4 through pipe L2 provided In upper section 41 of reactor 4.

In accordance with the production method in the present invention, ε-caprolactam can be produced from a raw material gas comprising cyclohexanone oxime with a high conversion of cyclohexanone oxime and a high selectivity to ε-caprolactam, for example, by utilizing a fluidized-bed reaction apparatus.

The invention being thus described, it will be apparent that the same may be varied in many ways. Such variations are to be regarded as within the spirit and scope of the invention, and all such modifications as would be apparent to one skilled in the art are intended to be within the scope of the following claims.

The entire disclosure of the Japanese Patent Application No. 2003-193390 filed on Jul. 8, 2003, including specification, claims, drawings and summary, are incorporated herein by reference in their entirety.

The present invention is described in more detail by following Examples, which should not be construed as a limitation upon the scope of the present invention.

EXAMPLES

Example 1

As shown in FIG. 1, a reaction apparatus 1 comprising porous gas diffusion plate 2 and catalyst layer 3 in reactor 4 was provided. The inner diameter and the height of reactor 4 were 1,000 mm and 6,000 mm, respectively. Porous gas diffusion plate 2 was in the shape of a disk-like plate and had holes 21 with a diameter of about 2 mm on the average. which was arranged at 27 mm interval from one another in square arrangement, as shown in FIG. 2a. The number of holes in the porous gas diffusion plate was 1,024. As shown in FIG. 3a, the respective holes 21 were positioned at the tip ends of shrouds 22, which were extended downward from approximately flat main body 20 of the gas diffusion plate. The depth (h22) and the inner diameter (d22) of the shrouds were 9 mm and 4.4 mm, respectively. The total open surface area of holes 21 in porous gas diffusion plate 2 was about 3,200 mm². The catalyst layer 3 was placed on porous gas diffusion plate 2 by packing 155 kg of solid catalyst particles 31. The solid catalyst particles 31 contained MFI zeolite as a main component and had a particle diameter of from 5 μm to 200 μm, wherein about 98% by weight of the particles had a diameter of from 10 μm to 100 μm, and the weight average particle diameter was 55 μm. The height (h3) of catalyst layer 3 was 35 cm.

A raw material gas was supplied from lower section 42 of reaction apparatus 1 through pipe L1. The raw material gas had been prepared by diluting a cyclohexanone oxime gas with a methanol gas (in the amount of 1.8 times by weight as much as the cyclohexanone oxime gas) and a nitrogen gas (in the amount of 0.2 times by weight as much as the cyclohexanone oxime gas). The supply rate of the raw material gas was adjusted to be 600 kg/hr (i.e., cyclohexanone oxime at 200 kg/hr). The raw material gas was supplied at a temperature of 320° C. and gauge pressure of 0.03 MPa (0.3 kgf/cm²). The temperature and pressure of catalyst layer 3 were maintained at a temperature of 380° C. and 0.1 MPa (absolute pressure), respectively. The reaction of cyclohexanone oxime was conducted in reactor 4 to provide a reaction gas containing ε-caprolactam, which was then recovered through pipe L2 from the upper part of reactor 4.

The resulting reaction gas was analyzed with gas chromatography to determine conversion of cyclohexanone oxime and selectivity to ε-caprolactam. The conversion of cyclohexanone oxime and the selectivity to ε-caprolactam were 99.99% and 96.31%, respectively, when the total amount of the supplied cyclohexanone oxime was 300 kg based on 1 kg of solid catalyst particles 31.

It is noted that, conversion of cyclohexanone oxime and selectivity to ε-caprolactam were calculated using the equations below:

Conversion of cyclohexanone oxime $(\%)=(1-B_0/A_0) \times 100$

Selectivity to ε-caprolactam $(\%)=B_C(A_0-B_0) \times 100$ wherein $A_0$ is a molar amount of cyclohexanone oxime in the raw material gas; and $B_0$ is a molar amount of cyclohexanone oxime remaining in the reaction gas; and $B_C$ is a molar amount of ε-caprolactam In the reaction gas.

Comparative Example 1

ε-Cprolactam was produced in the same manner as in Example 1 except for exchanging porous gas diffusion plate 2 with another porous gas diffusion plate. The porous gas diffusion plate was in the shape of a disk-like plate with shrouuds and had holes with a diameter of about 6 mm on the average, which was arranged at 76 mm interval from one another in square arrangement. The number of holes in the porous gas diffusion plate was 120. The respective holes were positioned at the tip ends of shrouds, which were extended downward from main body of the gas diffusion plate. The depth and the inner diameter of the shrouds were 15 mm and 13 mm, respectively. The total open surface area of holes in porous gas diffusion plate was about 3,400 mm². It is noted that this diffusion plate was designed in accordance with the method described in Published Document "Fluidized-Bed Handbook", Baifukan Publisher, p. 256–259 (1999)).

The resulting reaction gas was recovered and was analyzed. As a result, the conversion of cyclohexanone oxime and the selectivity to ε-caprolactam were 99.79% and 94.30%, respectively, when the total amount of the supplied cyclohexanone oxime was 300 kg based on 1 kg of solid catalyst particles.

What is claimed is:

1. A method for producing ε-caprolactam, the method comprising the step of introducing a gas comprising cyclohexanone oxime into a layer of solid catalyst particles through a plurality of holes of a gas diffusion plate so that the solid catalyst particles are brought into contact with the gas, while fluidizing the catalyst layer, wherein the holes have an average diameter of 3 mm or smaller.

2. The method according to claim 1, wherein the method is carried out using a reaction apparatus equipped with a porous gas diffusion plate having a number of holes with an average diameter of 3 mm or smaller and having a layer of solid catalyst particles placed on the porous gas diffusion plate, so that a raw material gas containing cyclohexanone oxime is supplied through the holes of the porous gas diffusion plate to the catalyst layer so as to bring the raw material gas into contact with the solid catalyst particles while fluidizing the catalyst layer.

3. The method according to claim 1, wherein the solid catalyst particles are zeolite particles.

4. The method according to claim 1, wherein 90% by weight of the solid catalyst particles have a diameter of from 5 μm to 100 μm.

5. The method according to claim 1, wherein interval between mutually neighboring holes is 0.5 cm to 25 cm.

* * * * *